United States Patent
Yamashita et al.

(10) Patent No.: US 10,746,723 B2
(45) Date of Patent: Aug. 18, 2020

(54) BLOOD TEST KIT AND BLOOD ANALYSIS METHOD

(71) Applicant: FUJIFILM Corporation, Tokyo (JP)

(72) Inventors: Seiji Yamashita, Ashigarakami-gun (JP); Haruyasu Nakatsugawa, Ashigarakami-gun (JP); Susumu Osawa, Tokyo (JP); Shinya Sugimoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 137 days.

(21) Appl. No.: 15/861,353

(22) Filed: Jan. 3, 2018

(65) Prior Publication Data

US 2018/0128806 A1 May 10, 2018

Related U.S. Application Data

(63) Continuation of application No. PCT/JP2016/070006, filed on Jul. 6, 2016.

(30) Foreign Application Priority Data

Jul. 6, 2015 (JP) .................. 2015-135068
Jul. 6, 2016 (JP) .................. 2016-133962

(51) Int. Cl.
*G01N 33/48* (2006.01)
*A61B 5/15* (2006.01)
(Continued)

(52) U.S. Cl.
CPC ... *G01N 33/4875* (2013.01); *A61B 5/150022* (2013.01); *A61B 5/150343* (2013.01);
(Continued)

(58) Field of Classification Search
CPC ......... G01N 33/4875; G01N 33/48707; G01N 33/487; G01N 33/483; G01N 33/48;
(Continued)

(56) References Cited

U.S. PATENT DOCUMENTS 4,510,621 A * 4/1985 Sak .................. A61L 2/26
206/438
9,002,863 B2 4/2015 Faughnan
(Continued)

FOREIGN PATENT DOCUMENTS

CN 102303750 A 1/2012
CN 202144348 U 2/2012
(Continued)

OTHER PUBLICATIONS

English Machine Translation of JP 2000-258315 Description, obtained on Aug. 20, 2019, from https://www.j-platpat.inpit.go.jp/s0100. (Year: 2019).*

(Continued)

*Primary Examiner* — Christine T Mui
(74) *Attorney, Agent, or Firm* — Sughrue Mion, PLLC

(57) ABSTRACT

An object of the present invention is to provide a blood test kit of which a component in a small volume of blood can be mailed in a safe state by controlling the influence of the outside temperature during the mailing, and a highly accurate blood analysis method in which coefficient of variation of a measurement value is reduced. According to the present invention, a blood test kit including a diluent solution for diluting a blood sample; a separating means for recovering blood plasma components from the diluted blood sample; a container for storing the blood plasma components recovered from the diluted blood sample; and a cold insulation means for cold-insulating the container, is provided.

18 Claims, 2 Drawing Sheets

(51) Int. Cl.
*G01N 33/487* (2006.01)
*G01N 1/28* (2006.01)
*G01N 33/49* (2006.01)
*G01N 1/00* (2006.01)
*G01N 1/38* (2006.01)
*G01N 33/66* (2006.01)
*G01N 33/96* (2006.01)
*G01N 1/10* (2006.01)

(52) U.S. Cl.
CPC .. *A61B 5/150351* (2013.01); *A61B 5/150755* (2013.01); *G01N 1/00* (2013.01); *G01N 1/28* (2013.01); *G01N 1/38* (2013.01); *G01N 33/48* (2013.01); *G01N 33/49* (2013.01); *G01N 33/491* (2013.01); *G01N 33/66* (2013.01); *G01N 33/96* (2013.01); *A61B 5/150206* (2013.01); *G01N 1/10* (2013.01)

(58) Field of Classification Search
CPC ........ A61B 5/150022; A61B 5/150015; A61B 5/150007; A61B 5/15
USPC .......................................................... 422/430
See application file for complete search history.

(56) References Cited

U.S. PATENT DOCUMENTS

| | | | |
|---|---|---|---|
| 2001/0055784 A1 | 12/2001 | Noda et al. | |
| 2002/0153316 A1 | 10/2002 | Nanba et al. | |
| 2003/0012701 A1 | 1/2003 | Sangha et al. | |
| 2011/0020195 A1* | 1/2011 | Luotola | A61B 10/0045 422/512 |
| 2013/0226032 A1* | 8/2013 | Mitsuhashi | A61B 5/15003 600/577 |
| 2013/0267469 A1 | 10/2013 | Matson | |
| 2014/0234828 A1 | 8/2014 | Pobitschka | |

FOREIGN PATENT DOCUMENTS

| | | |
|---|---|---|
| CN | 202244659 U | 5/2012 |
| CN | 103407696 A | 11/2013 |
| CN | 203392194 U | 1/2014 |
| CN | 103732269 A | 4/2014 |
| CN | 104743262 A | 7/2015 |
| JP | 2000-258315 A | 9/2000 |
| JP | 2001-330603 A | 11/2001 |
| JP | 2003-161729 A | 6/2003 |
| JP | 2003-279564 A | 10/2003 |
| JP | 2009-109196 A | 5/2009 |
| JP | 2009-122082 A | 6/2009 |
| WO | WO 2003/005039 * 1/2003 | ............. G01N 33/49 |

OTHER PUBLICATIONS

Kyowa Medex Co., Ltd, WO 03/005039 A1, English Machine Translation, obtained by STIC at the USPTO, obtained on Oct. 28, 2019, pp. 1-69. (Year: 2019).*
Office Action dated Sep. 11, 2018 from the Japanese Patent Office in counterpart Japanese Application No. 2016-133962.
Office Action dated Apr. 30, 2019 from the State Intellectual Property Office of People's Republic of China in Chinese application No. 201680039609.7.
Extended European Search Report dated Jul. 10, 2018 from the European Patent Office in counterpart European Application No. 16821430.2.
Nakayama, K., et al, "Assessment of accuracy of immediate blood separation method: a novel blood analysis strategy", Environmental Health and Preventive Medicine, vol. 16, No. 1, 2010, pp. 1-5, XP055484506.
International Search Report dated Oct. 4, 2016, issued by the International Searching Authority in Application No. PCT/JP2016/070006.
International Preliminary Report on Patentability with translation of Written Opinion dated Jan. 9, 2018, issued by the International Searching Authority in Application No. PCT/JP2016/070006.
Horita et al., "Establishment of Mail Medical Examination System Using Immediate Plasma Separating Device by the Self-Collection Blood—The Method of Dilution Ratio Calculation by Using Internal Standard for the Sample with Different Amount of Collecting Blood," The Japanese Journal of Clinical Pathology, Jul. 25, 2008, vol. 56, No. 7, pp. 577-583 (total 8 pages).
Office Action dated Nov. 28, 2019 from the State Intellectual Property Office of People's Republic of China in counterpart Chinese application No. 201680039609.7.
Office Action dated May 29, 2020, from the China National Intellectual Property Administration in CN Application No. 201680039609.7.

* cited by examiner

BLOOD TEST KIT AND BLOOD ANALYSIS METHOD

CROSS-REFERENCE TO RELATED APPLICATIONS

This application is a Continuation of PCT International Application No. PCT/JP2016/070006 filed on Jul. 6, 2016, which claims priority under 35 U.S.C § 119(a) to Japanese Patent Application No. 2015-135068 filed on Jul. 6, 2015 and Japanese Patent Application No. 2016-133962 filed on Jul. 6, 2016. Each of the above application(s) is hereby expressly incorporated by reference, in its entirety, into the present application.

BACKGROUND OF THE INVENTION

1. Field of the Invention

The present invention relates to a blood test kit and a blood analysis method for mailing a component of a small volume of blood self-collected by a subject to be tested in a safe state, and performing a blood test thereof.

2. Description of the Related Art

As blood collection, generally, there are general blood collection in which a qualified person such as a doctor collects blood from the vein using a syringe, and self-blood collection in which a subject to be tested pricks his finger and the like using a blood collection needle so as to collect blood.

The blood collected by the general blood collection is transported to a medical institution or a test institution in a sealed state in a blood collection container, and tests are performed therein. In a case where the blood is transported without separating blood cells and blood plasma, tests are performed after a medical institution or a test institution performs centrifugation to separate the blood into blood cells and blood plasma. In addition, in the self-blood collection which is performed by a subject to be tested, the collected blood is separated into blood cells and blood plasma by a separation membrane, and the blood is transported to a test lab in a separated state, and then tests are performed therein.

JP2001-330603A discloses a quantitative analysis method in which an amount of a target component to be analyzed in a sample is measured, an amount of a normal component originally and homeostatically present in the sample, other than the target component, is measured, a volume of the sample is determined from the amount of this normal component and a known concentration of the normal component in the sample, and therefore a concentration of the target component to be analyzed in the sample is determined from the volume of the sample and the amount of the target component to be analyzed.

JP2003-161729A discloses a method for testing a blood sample collected by self-blood collection, and specifically discloses a method for quantifying a component to be quantified in a biological specimen, the method including 1) step of preparing a specimen for quantification consisting of an unknown volume of a biological specimen containing a component to be quantified which is collected without quantifying the volume thereof, and a certain volume of an aqueous solution containing a certain amount of an indicator substance, 2) step of obtaining a dilution factor (a) of the biological specimen from a concentration ($C_1$) of the indicator substance in the aqueous solution of a certain volume which contains a certain amount of the indicator substance, and a concentration ($C_2$) of the indicator substance in the specimen for quantification, 3) step of obtaining a concentration (Y) of the component to be quantified in the specimen for quantification, and 4) step of determining the component to be quantified in the biological specimen from the dilution factor (a) of the biological specimen obtained in 2), and the concentration (Y) of the substance to be quantified in the specimen for quantification obtained in 3).

In addition, JP2009-122082A discloses that a small volume of blood is collected from a human or an animal using a blood dilution quantitative instrument, and after dilution of the blood, or without dilution, a certain volume thereof is supplied to another instrument or container or is directly supplied to a reagent. Furthermore, JP2009-109196A discloses a method for quantifying a concentration of a component to be quantified in a biological specimen by utilizing an absorbance of an indicator substance in an aqueous solution for dilution.

Meanwhile, in a case where a subject to be tested collects a blood sample, the blood is collected by using a lancet equipped with a small blade, and is used for quantifying a concentration of an arbitrary component in the blood, but generally, it is required to collect 100 µL of a blood sample.

SUMMARY OF THE INVENTION

In a method for analyzing blood by diluting the blood with a buffer solution, a biological component is stored in the buffer solution under the physiological condition of pH 7.4, and thus is excellent in stability during transportation, but because the influence of the outside temperature during mailing cannot be controlled, several sample components are affected by the influence thereof particularly in mailing during the summer, and therefore an increase or a decrease of a measurement value occurs, by which performing of a test at high accuracy was difficult. Particularly, because a small volume of blood collected by the self-blood collection is delivered to a blood analysis center and the like by a means of mailing and the like, there was a problem that a change in blood components during the delivery affects accuracy, and therefore accurate test results cannot be obtained. Accordingly, by only employing the method for determining a dilution factor described in JP2001-330603A and JP2003-161729A, it was difficult to perform a test at high accuracy in a case where the transportation is performed in such a condition.

The present invention is a blood test kit in which a small volume of blood is diluted with a diluent solution, a dilution factor is determined, and a component to be measured in blood is analyzed. An object to be solved is to provide a blood test kit of which a component in a small volume of blood can be mailed in a safe state by controlling the influence of the outside temperature during the mailing. Another object to be solved of the present invention is to provide a blood analysis method using the blood test kit, by which the influence of a temperature of a measurement value is suppressed.

As a result of intensive studies to solve the object described above, the inventors of the present invention have found that by providing a cold insulation means for cold-insulating the container in a blood test kit including a diluent solution for diluting a blood sample; a separating means for recovering blood plasma components from the diluted blood sample; and a container for storing the blood plasma components recovered from the diluted blood sample, it is possible to provide a blood test kit by which the above object is solved. Furthermore, as a result of analyzing a component to be measured by a blood analysis method with the above blood test kit, a dilution factor is determined by using a normal component homeostatically present in blood and/or a normal component (internal standard substance) in a diluent solution, the inventors of the present invention have found that blood analysis in which the influence of a temperature of a measurement value is suppressed can be performed at high accuracy. The present invention has been completed by the teaching described above. That is, according to the present invention, the following inventions are provided.

(1) A blood test kit, comprising: a diluent solution for diluting a blood sample; a separating means for recovering blood plasma components from the diluted blood sample; a container for storing the blood plasma components recovered from the diluted blood sample; and a cold insulation means for cold-insulating the container.

(2) The blood test kit according to (1), in which the cold insulation means includes a cold insulator and a cold insulated bag.

(3) The blood test kit according to (1) or (2), in which the cold insulation means further includes a storing member having a thickness of 35 mm or less, in which the container for storing the recovered blood plasma components is storable.

(4) The blood test kit according to any one of (1) to (3), further comprising a member for recoding a history of temperature.

(5) The blood test kit according to any one of (1) to (4), further comprising a manual describing a method for using the cold insulation means.

(6) The blood test kit according to any one of (1) to (5), in which the blood test kit is a blood test kit for analyzing a concentration of a target component in the blood sample by using a normal component homeostatically present in blood, and the diluent solution does not contain the normal component.

(7) The blood test kit according to (6), in which the normal component is sodium ions or chloride ions.

(8) The blood test kit according to (6) or (7), in which the normal component is sodium ions or chloride ions, and at least one normal component.

(9) The blood test kit according to (8), in which the at least one normal component is a normal component selected from total protein or albumins.

(10) The blood test kit according to (8) or (9), in which the blood test kit is a blood test kit for analyzing a concentration of the target component in the blood sample by using the normal component homeostatically present in blood, and verifying the analysis, and the diluent solution does not contain the normal component.

(11) The blood test kit according to any one of (1) to (10), in which the diluent solution contains a normal component not present in blood, and the blood test kit is a blood test kit for analyzing a concentration of the target component in the blood sample by using the normal component not present in blood.

(12) A blood analysis method using the blood test kit according to any one of (6) to (9), the method comprising: recovering blood plasma from a blood sample; diluting the recovered blood plasma with a diluent solution; determining a dilution factor of the blood plasma by using a normal component homeostatically present in blood, which is contained in the diluted blood plasma; and analyzing a concentration of a target component in the blood sample.

(13) A blood analysis method using the blood test kit according to (10), the method comprising: recovering blood plasma from a blood sample; diluting the recovered blood plasma with a diluent solution; determining a dilution factor of the blood plasma by using a normal component homeostatically present in blood, which is contained in the diluted blood plasma; analyzing a concentration of a target component in the blood sample; determining the dilution factor of the blood plasma by using a normal component different from the normal component homeostatically present in blood; and verifying the analysis of a concentration of the target component.

(14) A blood analysis method using the blood test kit according to (11), the method comprising: recovering blood plasma from a blood sample; diluting the recovered blood plasma with a diluent solution; determining a dilution factor of the blood plasma by using a normal component not present in blood, which is contained in the diluted blood plasma; and analyzing a concentration of a target component in the blood sample.

(15) A blood analysis method using the blood test kit according to (11) which includes the diluent solution not containing the normal component homeostatically present in blood, the method comprising: recovering blood plasma from a blood sample; diluting the recovered blood plasma with the diluent solution; determining a dilution factor of the blood plasma by using a normal component homeostatically present in blood, and a normal component not present in blood which is contained in the diluted blood plasma; and analyzing a concentration of a target component in the blood sample.

(16) The blood analysis method according to any one of (12) to (15), in which a liquid volume of the diluted blood plasma is 100 μL or more and 1000 μL or less.

According to the blood test kit of the present invention, a component in a small volume of blood can be mailed in a safe state, and therefore blood analysis in which the influence of a temperature of a measurement value is suppressed can be performed at high accuracy.

DESCRIPTION OF THE PREFERRED EMBODIMENTS

Figure 1:
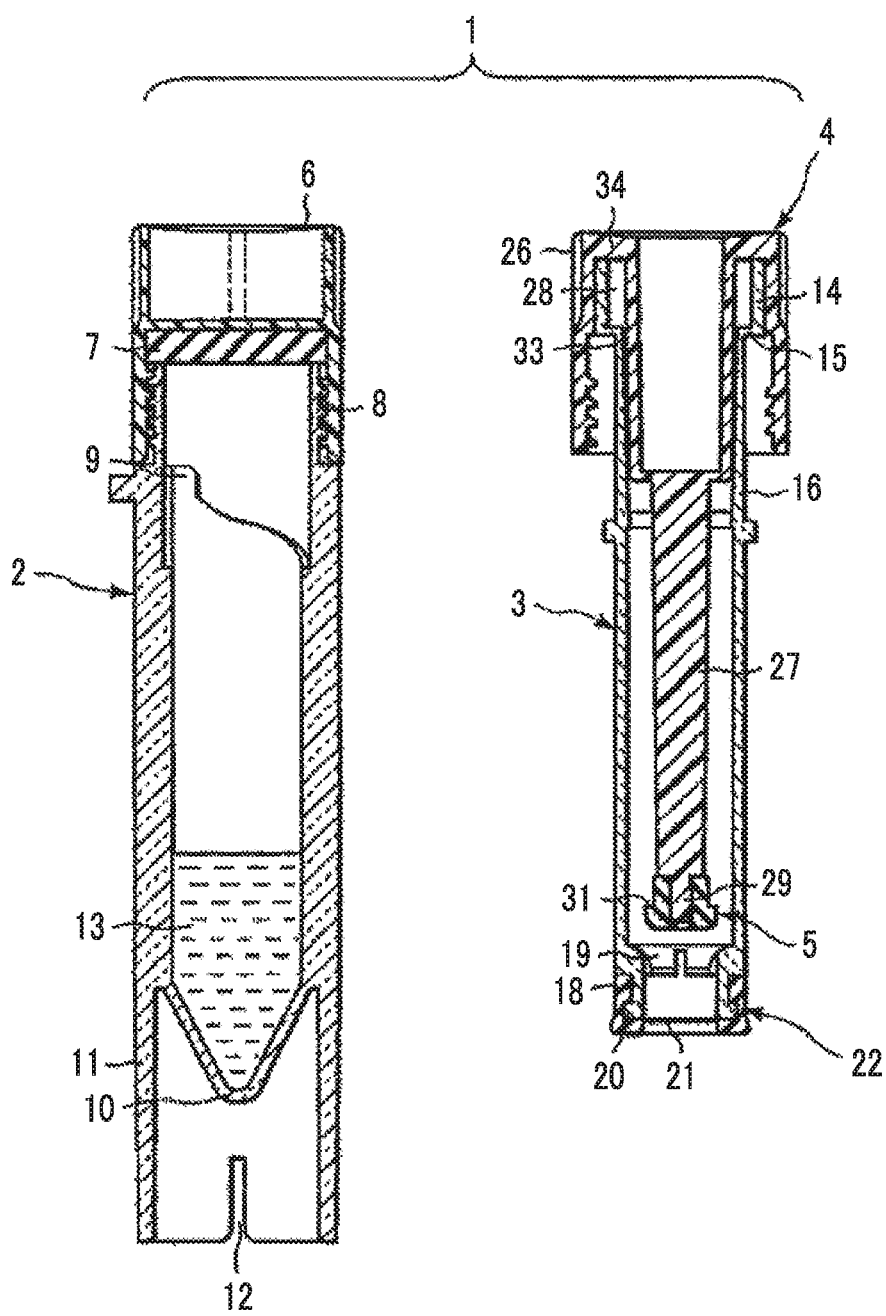
FIG. 1 illustrates an example of a configuration of a container for storing blood plasma components recovered from a diluted blood sample.

Hereinafter, the present invention will be described in detail.

A normal component homeostatically present in the blood refers to an external standard substance or an external standard.

A normal component not present in the blood refers to an internal standard substance or an internal standard.

There is a case where a patient or a subject to be tested moves to a medical institution or a test lab so that blood is collected and a test is performed for medical treatment or diagnosis of diseases, or health management. It is necessary to wait for a long period of time in order to know the result of the test, and there is a case where blood collection from the vein may be a burden depending on the child. In addition, including a movement for a test, half a day more is required, and there was a problem of losing the opportunity to undergo a test due to circumstances of their own work and the like, and a problem of occurrence of inconvenience on their work. The above problems are solved by making it possible for a patient or a subject to be tested to perform self-blood collection to collect a small volume of blood at home, a test room, and the like, and to stably store and transport the blood. For example, JP2001-330603A and JP2003-161729A describe a method for testing a blood sample separated from the self-blood collection.

Examples of a component homeostatically present in blood as a normal component include sodium ions ($Na^+$), chloride ions ($Cl^-$), potassium ions ($K^+$), magnesium ions ($Me^+$), calcium ions ($Ca^{2+}$), total protein (TP), and the like. In order to detect the above normal component at sufficiently high accuracy in a case where a small volume of blood component is diluted with a high dilution factor, it is preferable to measure a normal component present in a small volume of blood at a high concentration. As such a normal component, sodium ions ($Na^+$) or chloride ions ($Cl^-$) are preferable, and among components homeostatically present in the blood, sodium ions ($Na^+$) which is present in blood at a highest amount is most preferable. Meanwhile, a method for absorbing blood into a filter paper or a porous material, drying the blood so as to be mailed, and extracting blood components may degrade components during drying process or at the time of the mailing. Furthermore, according to JP2003-161729A, as a buffer solution for extracting a biological component from a dried specimen, it is necessary to use a buffer solution to which NaOH, NaCl, or HCl is added in order to adjust the pH and stabilize the biological component. Therefore, concentrations of sodium ions and chloride ions which are the most homeostatic components in the specimen and have little difference between individuals, cannot be used as an external standard, which is for correcting a concentration of another biological component of the diluted specimen.

In addition, JP2003-161729A discloses a method for accurately determining a dilution factor of blood by providing an internal standard substance in a buffer solution in a case of diluting with a buffer solution.

On the other hand, in a method for diluting the blood with a buffer solution, a biological component is stored in the buffer solution under the physiological condition of pH 7.4, and thus is excellent in stability during transportation by mailing and the like, but because the influence of the outside temperature during mailing cannot be controlled, several sample components are affected by the influence thereof particularly in mailing during the summer, and therefore an increase or a decrease occurs, by which performing of a test at high accuracy was difficult. Particularly, because a small volume of blood collected is delivered to a blood analysis center and the like by a means of mailing and the like, there was a problem that a change in blood components during the delivery affects accuracy, and therefore accurate test results cannot be obtained. Accordingly, in this situation, it is difficult to carry out long-term transportation for one week or more merely by determination of a dilution factor by an external standard substance described in JP2001-330603A, and determination of a dilution factor by an internal standard substance described in JP2003-161729A.

In the present invention, a component to be measured is analyzed by a blood analysis method using a blood test kit having a cold insulation means for cold-insulating a container, the method including determining a dilution factor using a normal component homeostatically present in blood (external standard substance) and/or a normal component (internal standard substance) in a diluent solution, and it was found that it is possible to reduce variations in a measurement value and to enable highly accurate blood analysis. The use of the cold insulation means, and the normal component homeostatically present in blood and/or the normal component in a diluent solution in combination has not been known at all in the related art, and it is not expected at all that highly accurate blood analysis became possible by the above combination.

According to the blood test kit and the blood analysis method of the present invention, in a case where a patient performs self-blood collection, for example, during the summer or in a high-temperature and humidity region, even in a state in which an increase or a decrease of a measurement value is likely to occur due to the influence of the outside temperature during mailing on a component to be measured, it is possible to easily control the influence of the outside temperature during mailing, the variations in the component to be measured is suppressed, and therefore highly accurate test is possible. The collection of a small volume of blood using the blood test kit of the present invention is not limited by time and place, and can be applied to cases where there is no time to go to a medical institution, disaster, telemedicine, health management, and the like. Regarding a presymptomatic patient, a disease can be found at an early stage, and thus this blood collection contributes to save medical expenses. Furthermore, according to the present invention, it is possible to perform various tests such as biochemical test of 13 items, tumor markers, and hepatitis tests by using a small volume of blood (for example, 65 µl). In addition, a large amount of a specimen can be efficiently measured with a commercially available biochemical/automated immunoassay analyzer. The test data measured using the blood test kit of the present invention is sent to a smartphone, and therefore can be used for a system for health management on a daily basis and early detection of diseases.

[1] Blood Test Kit

The blood test kit of the present invention includes a diluent solution for diluting a blood sample; a separating means for recovering blood plasma components from the diluted blood sample; a container for storing the blood plasma components recovered from the diluted blood sample; and a cold insulation means for cold-insulating the container.

(1) Diluent Solution for Diluting Blood Sample

The blood test kit of the present invention is for performing analysis of a target component to be measured, in which a patient performs blood collection and transports the blood to a medical institution or a test institution, and there is a possibility that the blood is left alone for a long period of time from the blood collection to the analysis. During this time, it is preferable to prevent decomposition or denaturation of the target component in the diluent solution of blood. A pH of blood is generally maintained constant at a pH of about 7.30 to 7.40 for healthy subjects. Accordingly, in order to prevent decomposition or denaturation of the target component, the diluent solution preferably has pH 6.5 to pH 8.0, more preferably pH 7.0 to pH 7.5, and further preferably pH 7.3 to pH 7.4, and is preferably a buffer solution containing a buffering component for suppressing variation in pH.

As the type of the buffer solution, there are an acetate buffer solution (Na), a phosphate buffer solution (Na), a citrate buffer solution (Na), a borate buffer solution (Na), a tartrate buffer solution (Na), a Tris (tris(hydroxymethyl)

aminoethane buffer solution (Cl), a HEPES ([2-[4-(2-hydroxyethyl)-1-piperazinyl]ethanesulfonic acid]) buffer solution, a phosphate buffered saline (Na), and the like. Among these, as a buffer solution around pH 7.0 to pH 8.0, a phosphate buffer solution, a Tris buffer solution, and a HEPES buffer solution are representative. However, the phosphate buffer solution contains a sodium salt of phosphoric acid. The Tris buffer solution has a dissociation pKa (Ka is an acid dissociation constant) of 8.08, and therefore these solutions are usually used in combination with hydrochloric acid for maintaining buffering ability around pH 7.0 to pH 8.0. A dissociation pKa of a sulfonic acid of HEPES is 7.55, but in order to adjust buffer solution at constant ionic strength, a mixture of sodium oxide and sodium chloride with HEPES is used. Therefore, these solutions are useful as a buffer solution having an action of maintaining pH constant but contain sodium ions or chloride ions which are substances preferably used as an external standard substance in the present invention, and therefore, application thereof to the present invention is not preferable. Therefore, the present inventors have conducted intensive studies and have found a new buffer solution not containing sodium ions and chloride ions.

The diluent solution which does not contain sodium ions and chloride ions and can be used in the present invention is preferably a diluent solution including at least an amino alcohol compound selected from the group consisting of 2-amino-2-methyl-1-propanol (AMP), 2-ethylaminoethanol, N-methyl-D-glucamine, diethanolamine, and triethanolamine, and at least one buffering agent selected from the group consisting of 2-[4-(2-hydroxyethyl)-1-piperazinyl]ethanesulfonic acid (pKa=7.55) also called HEPES which is a buffering agent having a pKa of around 7.4, N-tris(hydroxymethyl)methyl-2-aminoethanesulfonic acid also called TES (pKa=7.50), 3-morpholinopropanesulfonic acid also called MOPS (pKa=7.20), and N,N-bis(2-hydroxyethyl)-2-aminoethanesulfonic acid also called BES (pKa=7.15), which are Good's buffer solutions (Good's buffers). Among these, a combination of 2-amino-2-methyl-1-propanol (AMP) with HEPES, TES, MOPS, or BES is preferable, and a combination of 2-amino-2-methyl-1-propanol (AMP) with HEPES is most preferable.

For producing the buffer solution described above, an amino alcohol may be mixed with the Good's buffer solutions at a concentration ratio of 1:2 to 2:1, preferably 1:1.5 to 1.5:1, and more preferably 1:1. A concentration of the buffer solution is not limited, but a concentration of the amino alcohol or the Good's buffer solution is 0.1 to 1000 mmol/L, preferably 1 to 500 mmol/L, and more preferably 10 to 100 mmol/L.

A chelating agent, a surfactant, an antibacterial agent, a preservative, a coenzyme, a saccharide, and the like may be contained in the buffer solution in order to keep a target component to be analyzed stable. Examples of the chelating agent include a salt of ethylenediaminetetraacetic acid (EDTA), citrate, oxalate, and the like. Examples of the surfactant include a cationic surfactant, an anionic surfactant, an amphoteric surfactant, and a nonionic surfactant. Examples of the preservative include sodium azide, antibiotics, and the like. Examples of the coenzyme include pyridoxal phosphate, magnesium, zinc, and the like. Examples of the saccharide of a red blood cell-stabilizing agent include mannitol, dextrose, oligosaccharide, and the like. Particularly, by adding the antibiotics, it is possible to suppress the growth of bacteria which are partially mixed from the surface of the finger at the time of collecting blood from the finger, suppress degradation of biological components by bacteria, and stabilize the biological components.

The components diluted with these buffer solutions do not interfere with the measurement even in various measuring methods by a biochemical/automated immunoassay analyzer. Furthermore, the components are preferable because blood cells are not hemolyzed, and biological components can be stored as stable as possible even at 37° C.

In a case where whole blood is used as a biological specimen, filtration of blood cell components in a diluted blood through a filter is required, and by setting osmotic pressure of the buffer solution equivalent to blood (285 mOsm/kg (mOsm/kg: an osmotic pressure that 1 kg of water of the solution has, and indicates millimoles of ions)) or more, it is possible to prevent hemolysis. The osmotic pressure can be adjusted to be isotonic by measurement of a target component, salts which do not affect a normal component homeostatically present in the blood, sugars, buffering agents, and the like.

A first example of the diluent solution for diluting the components of a blood sample is a diluent solution not containing a substance homeostatically present in the blood (hereinafter, will also be referred to as "homeostatic substance") used for obtaining a dilution factor. The phrase "does not contain" in the present specification means the solution "substantially does not contain". The phrase "substantially does not contain" means that the solution does not contain a homeostatic substance used for obtaining a dilution factor at all, or even if the homeostatic substance is contained, this means a case where an ultra-small volume of concentration is contained to the extent that does not affect measurement of a homeostatic substance in a diluent solution after diluting a blood sample. In a case where sodium ions or chloride ions are used as a homeostatic substance, a diluent solution which substantially does not contain sodium ions or chloride ions is used as a diluent solution.

In a case where the blood test kit of the present invention is a blood test kit for analyzing a concentration of a target component in a blood sample using normal components homeostatically present in the blood, a diluent solution is a diluent solution not containing above normal components.

A second example of a diluent solution for diluting components of a blood sample is a diluent solution containing an internal standard substance. The internal standard substance can be added to the diluent solution used for diluting a biological specimen so as to have a predetermined concentration. As the internal standard substance, it is possible to use a substance which is not contained in the blood sample at all, or is contained thereto but in an ultra-small amount. As the internal standard substance, it is preferable to use substances which do not interfere with the measurement of the target component in the blood sample, substances which do not decompose under the action of biological enzymes in the blood sample, substances which are stable in the buffer solution, substances which do not pass through a blood cell membrane and not contained in the blood cells, substances not adsorbed in a container storing the buffer solution, and substances which can be utilized by a detection system capable of measurement at high accuracy.

As the internal standard substance, a substance which is stable even if the substance is stored for a long period of time in a state of being added to a diluent solution which is a buffer solution, is preferable. Examples of the internal standard substance include glycerol 3-phosphate, Li, Rb, Cs, or Fr as alkali metal, and Sr, Ba, or Ra as alkaline earth metal. Among these, glycerol 3-phosphate or Li is preferable. These internal standard specimens can develop color by adding a second reagent at the time of measuring a concentration after blood dilution, and the concentration in the diluted blood can be obtained from color optical density. For example, measurement of lithium of an internal standard substance added to a buffer solution is carried out by the chelate colorimetric method (halogenated porphyrin chelating method: perfluoro-5,10,15,20-tetraphenyl-21H,23H-porphyrin) using an automatic biochemistry analyzer, and it is possible to easily measure a large number of specimens of a small amount.

In a case where the blood test kit of the present invention is a blood test kit for analyzing a concentration of the target component in the blood sample by using normal components not present in the blood, a diluent solution is diluent solution which contains the above normal components not present in the blood.

A third example of a diluent solution for diluting a blood sample is a diluent solution not containing normal components homeostatically present in the blood, which are used for obtaining a dilution factor, and containing an internal standard substance.

(2) Separating means for recovering blood plasma components from diluted blood sample and container for storing blood plasma components recovered from diluted blood sample As the separation means for recovering blood plasma components from a diluted blood sample, an aspect of a separation membrane is preferable, and a filter having fine pores capable of separating blood cell components is more preferable.

A shape and a size of the container for storing blood plasma components recovered from a diluted blood sample are not particularly limited.

The material of the container is preferably a synthetic resin from the viewpoints of difficulty in breakage, sanitation, price, and the like. Examples thereof include polyethylene, polypropylene, polyvinyl chloride, polyvinylidene chloride, polystyrene, polyvinyl acetate, polyurethane, polyethylene terephthalate, polylactic acid, acrylonitrile butadiene styrene resin (ABS resin), acrylonitrile styrene resin (AS resin), acrylic resin (PMMA), polycarbonate, silicone resin, silicone rubber, and the like.

As the example of the blood test kit of the present invention, the kit can include a diluent solution for diluting a blood sample, a first storing instrument in which the diluent solution is stored, a separation means for separating and recovering blood plasma from the blood sample diluted with the diluent solution, a holding instrument for holding the separating instrument, a second storing instrument for storing the recovered blood plasma, a sealing instrument for maintaining the stored blood plasma in the second storing instrument, a needle or a lancet for pricking the skin to allow blood to flow out of the skin, a strip of bandage or a sterile swab to be put on the wound (for example, nonwoven fabrics impregnated with isopropanol (70% by mass isopropanol and the like), ethanol, or the like), an instruction manual, and the like.

As the first storing instrument and the second storing instrument, one instrument may be used as both the first storing instrument and the second storing instrument, or an embodiment in which instruments are provided separately may be used. The first storing instrument and the second storing instrument is preferably made of a transparent material such that a patient or a measurer who performs measurement of a dilution factor or analysis of a target component to be analyzed can confirm a diluent solution in the storing instrument by which the blood is diluted. The term "transparent" referred in the present invention may be transparent to the extent that the observer can confirm a volume of the solution therein, and is a concept including translucence and the like.

As the holding instrument for holding the separating instrument, an aspect of a gasket is preferable. In addition, as the sealing instrument, in a case where the storing instrument is an instrument having a tubular shape, and the like, it is possible to use a cap capable of being used as a lid for the opening, a lid having a helical groove, a rubber closure, and the like.

As a specific configuration example of the first storing instrument in which a diluent solution is stored, the separating instrument for separating and recovering blood plasma from a blood sample diluted with the diluent solution, the holding instrument for holding the separating instrument, the second storing instrument for storing the recovered blood plasma, and the sealing instrument for keeping the blood plasma in the second storing instrument, it is possible to use instruments described in FIG. 1 to FIG. 13 of JP3597827B, for example. FIG. 1 of JP3597827B is incorporated as FIG. 1 of the present application.

A blood separating instrument 1 includes a blood collection container 2 (first storing instrument in which a diluent solution is stored), a tubular body 3 capable of being to fit into the blood collection container 2 so as to be inserted (second storing instrument for storing recovered blood plasma), a cap piston 4 capable of being capped on the tubular body 3, and a sealing lid 5 (sealing instrument) provided at a lower end of the cap piston 4. Before use, an upper end opening portion of the blood collection container 2 is sealed by a cap 6 via a packing 7, as shown in FIG. 1. A container for storing a diluted blood sample of the present invention corresponds to a combination of the blood collection container 2 and the tubular body 3 in the configuration of FIG. 1. That is, the container for storing a diluted blood sample may be one or a combination of two or more thereof.

The blood collection container 2 is made of a transparent material and has a cylindrical shape. At the upper end portion thereof, a screw portion 8 is formed on the outer surface, and a locking portion 9 is protruded toward the inner surface. In addition, at a lower end portion of the blood collection container 2, a bottom portion 10 having an inverted conical shape is formed, and a cylindrical leg portion 11 is formed around the bottom portion 10. The leg portion 11 has the same outer diameter as a sample cup used at the time of an analytical test of blood, and at positions opposite to the lower end thereof, slit grooves 12 are preferably formed in a vertical direction, respectively. Furthermore, a predetermined volume, for example, 500 mm$^3$ of a diluent solution 13 may be put in the blood collection container 2 in advance, as shown in FIG. 1.

The tubular body 3 is made of a transparent material and has a cylindrical shape, and at an upper end portion thereof, an expanded diameter section 14 is formed. The expanded diameter section 14 is connected to a main body portion 16 via a thin portion 15. A reduced diameter section 18 is formed at the lower end portion of the tubular body 3, and a protruded locking portion 19 is formed on the inner surface of the reduced diameter section 18. Furthermore, at a lower end portion of the reduced diameter section 18, an outer flange portion 20 (holding instrument) is formed, a lower end opening portion of the outer flange portion 20 is covered with a filtration membrane 21 (separating instrument), and the filtration membrane 21 allows blood plasma in the blood to pass through and prevents passage of the blood cells.

A cover 22 made of silicone rubber is attached to the outer periphery of the reduced diameter section 18 (FIG. 1).

The cap piston 4 is constituted by a substantially cylindrical knob portion 26 and a mandrel portion 27 concentric with the knob portion 26 and extending downward. At an inner upper end portion of the knob portion 26, a cylindrical space 28 into which the expanded diameter section 14 of the tubular body 3 is capable of being fitted to be inserted is formed, and the knob portion is threaded in a lower portion into which a screw can screw. The mandrel portion 27 has a lower end portion 29 formed in a pin shape, and a sealing lid 5 is detachably provided on the lower end portion 29 (refer to FIG. 1). The sealing lid 5 is made of silicone rubber.

A method for separating blood by the instruments described above is described in detail in paragraphs 0023 to 0026 and FIG. 12 and FIG. 13 of JP3597827B, the contents of which are incorporated in the present specification.

(3) Cold Insulation Means for Cold-Insulating Cool

A preferable temperature at the time of mailing a blood sample is −10° C. or more and 20° C. or less, and particularly preferable temperature is 0° C. or more and 10° C. or less. In the present invention, it is possible to achieve the cold insulation by including the cold insulation means in the blood test kit.

As the cold insulation means, a cold insulator can be used. On the surface of a bag containing the cold insulator or on a manual, it may be described that the cold insulator is cooled in a freezer or the like in advance, and the cooling time until the cold insulator becomes a state capable of cold insulation, and the like. In addition, a method for using a cold insulation member storing the cold insulator and recovered blood plasma components may be described. Based on this, a person who collects blood can perform blood collection in consideration of the cooling time, and can store the blood sample in a predetermined cold insulation member. The cold insulator is not particularly limited, but as examples thereof, there are sodium chloride, ammonium chloride, magnesium chloride, and the like as an aqueous solution of an inorganic salt; ethylene glycol, propylene glycol, and the like as a polyhydric alcohol; and a hydrophilic polymer such as carboxy methyl cellulose, polyvinyl alcohol, sodium polyacrylate, polyacrylamide, and the like as a gelling agent. As a nucleating agent for freezing the cold insulator, it is possible to use an agent to which silver iodide, copper sulfide, xanthan gum, α-phenazine, and sodium pyrophosphate are added, and the like. Particularly, the cold insulator (for example, product name: ICEPAK, registered trademark) which is generally put into a bag so as to be used and is commercially available has about 99% water and high water-absorption resin (sodium polyacrylate), a preservative, and a shape stabilizer. The insulator represents no cold-insulating effect in a state of being melted at room temperature, and thus is used after being sufficiently frozen in a freezer. Even after the insulator is used and becomes warm, it is possible to use the insulator repeatedly many times just by freezing.

The dilution with a buffer solution and the subsequent separation and recovery of blood plasma are important for reducing the hemolysis of blood cells and the influence of the elution of a substance from blood cells. By the cold insulation in this case, the influence of a substance in the buffer solution on blood plasma components can be minimized. In terms of maintaining the stability of a target blood component, the cold insulation is aimed to realize stabilization of the state after blood plasma separation, and produces a synergistic effect on stabilization by designing an appropriate buffer solution (diluent solution).

A container for storing a sample in a solution state, in which a small volume of blood used for a blood test is diluted with a diluent solution, or a container for storing a sample in which blood plasma and blood cells are separated immediately after collecting and diluting the blood are preferably covered or surrounded with the cold insulator in a state capable of cold insulation. Furthermore, it is preferable to put the container in a cold insulated bag having a metal foil such as an aluminum film having heat shielding property from the viewpoint of prolonging the cooling time of the cold insulator, and from the viewpoint of preventing the temperature from increasing, which occurs due to the light absorption by the blocking of external light. That is, the cold insulator means is preferably composed of the cold insulator and the cold insulated bag. In addition, covering the container with a heat insulating sheet after covering or surrounding with the cold insulator, and then putting the container in a cold insulated bag for thermal insulation having a metal foil such as an aluminum film, is particularly preferable from the viewpoint of prevention of cold air leakage of the cold insulator. In addition, it is preferable that the structure thereof also has an effect of alleviating shock caused by transportation as well as cold insulation.

For a person who collects blood, even if the container is covered with the cold insulator in the above manner and is in a state of being put in the cold insulated bag, if the container becomes a size which cannot be mailed unless the person goes to the window of the post office to go through a procedure, this may become a factor for avoidance of using the kit for collecting a small volume of blood of the present invention in a case where it is far from the nearest post office or in a case of an elderly person.

For the above reason, it is preferable that the size be insertable into a mailbox. For example, if the container is a post packet (size 340 mm×250 mm×thickness 35 mm, weight 1 kg or less), there is no need to go to the window of the post office and the container can be put directly into the mailbox. Moreover, the container can be transported at low cost, and there is also a mail tracking service, which are preferable in terms of price and security.

As measure for limiting the thickness within 35 mm, for example, a storing member for storing a container having a sample having a thickness of 35 mm or less is included in the blood test kit as one of the cold insulation means, and at the time of cooling the cold insulator in advance, by sandwiching this container with the cold insulator, a space for storing the container having the sample can be secured in the storing member even when the cold insulator is solidified and hardened so as to be able to perform cold insulation. Therefore, it is possible to achieve the thickness of 35 mm or less in total thickness even if the container having the sample is sandwiched with the hardened cold insulator.

In addition, as another preferred embodiment of the present invention, by covering a container in which blood plasma components after blood cells/blood plasma separation are stored by using cold insulator having a two-layer structure of a portion where the cold insulator is solidified through cooling and a portion that is not solidified, it is possible to realize a thickness of 35 mm or less, and it is possible to mail the container easily and inexpensively.

(4) Other Components

A preferred embodiment of the blood test kit of the present invention is an embodiment having a member for recording the temperature history after using the cold insulation means. As a member for recording the temperature history, it is preferable to use a thermo label or an RFID (radio frequency identifier) tag, and the like. By attaching an appropriate temperature-detectable thermo label and the like to the container having a sample, it is possible to check the maximum reached temperature before and after arrival at an analysis center, by which the state of the cold insulation effect during mailing can be understood. Alternatively, by arranging the RFID tag on which a temperature sensor is mounted in the vicinity of the container storing the blood sample, it is possible to manage the temperature change at the time of mailing in detail at the analysis center.

In addition, in order to use the cold insulator again, it is preferable that the bag to which the cold insulator was put is cleanable, and the surface thereof is subjected to antimicrobial coating and the like.

A preferred embodiment of the blood test kit of the present invention includes an embodiment including a manual that describes a method for using the cold insulation means. For example, a kit including an item for determining whether or not to use the cold insulator at the time of mailing is also a preferred embodiment. For example, when the thermo label is put in the kit and the reached temperature of a reversible thermo label before mailing is 25° C. or higher (during summer in a hot and humid region), the kit having the manual describing the instruction to use the cold insulator is preferable. In addition, the kit also contains an irreversible thermo label that can be used by peeling off the release paper, and at the time of mailing, it is possible to understand the highest reached temperature at the time of mailing after blood collection by packing the diluted blood and the irreversible thermo label which has been started to be used together. Therefore, in a case of purchasing the kit in the summer, collecting blood at the period of low temperature in the winter and mailing the blood, or in a case of storing the kit in a place that is exposed to direct sunlight, and the like, the maximum reached temperature at the time of mailing after blood collection can be appropriately checked, which is preferable.

(5) Form of Providing Blood Test Kit

The number of various components contained in the blood test kit of the present invention is not particularly limited, and each component may be one, or there may be a plurality of, for example, 2 or more of the components.

The blood test kit of the present invention can provide a diluent solution for diluting a blood sample, a separating means for recovering blood plasma components from the diluted blood sample, a container for storing the blood plasma components recovered from the diluted blood sample, and a cold insulation means for cold-insulating the container, in a manner of being stored in the storing container for storing these.

[2] Blood Analysis Method

By collecting a blood sample using the blood test kit of the present invention, it is possible to measure a component to be analyzed in a blood sample.

The blood analysis method of the present invention may be carried out by self-blood collection in which a subject to be tested collects the blood by himself, or may be carried out by general blood collection in which a qualified person such as a doctor collects the blood using a syringe.

In the present invention, a biological specimen which is an analysis target is blood, and the blood is a concept including serum or blood plasma. Preferably, it is possible to use blood plasma or serum obtained by collecting a small volume of blood from the subject to be tested, diluting the blood with a buffer solution, and then separating blood cells through a filter or by centrifugation.

The origin of a blood sample is not limited to humans, and may be an animal other than humans (mammals, birds, fish, and the like), and the like. Examples of the animal other than humans include horses, cows, pigs, sheep, goats, dogs, cats, mice, bears, pandas, and the like. The origin of a blood sample is preferably humans.

As a preferred embodiment, a patient himself pricks a fingertip and the like using a blade-attached instrument such as a lancet and then collects the blood flowing out of the skin. It is preferable that the blood is collected in a manner of reducing the invasiveness so to alleviate the burden on a patient, and when collecting the blood, it is desirable to be able to collect the blood with little pain or painlessly. In this case, it is desired that a depth and a size of the wound are small, and therefore, a volume of blood collected from a patient, which is set for the analysis method of the present invention is preferably 100 µl or less in consideration of burden on a patient. In addition, a liquid volume of diluted blood plasma after diluting with a diluent solution is preferably 100 µL, or more and 1000 µL, or less. With a volume of 100 µL, or more, the frequency of hemolysis at the time of plasma separation decreases, and even in a case where it takes time to mail, there is no restriction such as requiring a highly airtight container. With a volume of 1000 µL, or less, an effective dilution ratio can be realized for measurement, and therefore measurement at high accuracy becomes possible.

In a first embodiment of the blood analysis method of the present invention, a component homeostatically contained in a blood sample is used as a normal component. Specific examples thereof include sodium ions ($Na^+$), chloride ions ($Cl^-$), potassium ions (10, magnesium ions ($Me^+$), calcium ions ($Ca^{2+}$), total protein ("TP"), albumins, and the like. As a concentration of these normal components contained in a blood sample, a concentration of Na is 134 to 146 mmol/litre (average value: 142 mmol/litre), a concentration of Cl is 97 to 107 mmol/litre (average value: 102 mmol/litre), a concentration of K is 3.2 to 4.8 mmol/litre (average value: 4.0 mmol/litre), a concentration of Mg is 0.75 to 1.0 mmol/litre (average value: 0.9 mmol/litre), a concentration of Ca is 4.2 to 5.1 mmol/litre (average value: 4.65 mmol/litre), a concentration of total protein is 6.7 to 8.3 g/100 mL (average value: 7.5 g/100 mL), a concentration of albumins is 4.1 to 5.1 g/100 mL (average value: 4.6 g/100 mL). Among these, when the blood components of a small amount are diluted with a high dilution factor, in order to detect the homeostatic normal components therein at sufficiently high accuracy, it is preferable to measure a standard substance present in the blood at a high concentration. In addition, it is considered that even in a case in which unintended components other than blood are mixed in a diluent solution, the standard substance present in the blood at a high concentration is highly resistant to the influence of contamination and can suppress a deterioration of the test accuracy. As such normal components, sodium ions or chloride ions is preferable, and among the normal components homeostatically present in the blood, sodium ions which are present in the blood at a highest amount are most preferable. Na ions have a standard value (normal value) of 142 mmol/liter, accounting for 90% or more of total cations in the blood plasma.

In the blood analysis method of the first embodiment described above, blood plasma is recovered from a blood sample using a blood test kit including a diluent solution not containing the normal components homeostatically present in the blood, the recovered blood plasma is diluted with the diluent solution, and using the normal components homeostatically present in the blood, a dilution factor of the diluted blood plasma is determined, and therefore it is possible to analyze a concentration of a target component in the blood sample.

A concentration of sodium ions and a concentration of chloride ions can be measured by, for example, the flame photometric method, the atomic absorption method, the glass-electrode method, the titration method, the ion selective electrode method, the enzyme activity method, and the like.

In the present invention, a specimen obtained by collecting a small volume of blood from a finger and diluting the blood with a buffer solution is only about 150 µl, and it is preferable that measurement of an external standard substance can be performed with a small volume of several µl because 10 or more items of biochemical components and immunological test items are measured. In addition, since it is necessary to analyze a large number of specimens, it is preferable that application thereof to a commercially available biochemical/automated immunoassay analyzer is possible.

In the present invention, a preferred standard substance is sodium ions, and a dilution factor (Y/X) of a blood sample is calculated from a measurement value (concentration X) of sodium ions in a diluent solution after diluting the blood, and a known concentration value (concentration Y; 142 mmol/liter) of sodium ions, which is a normal component of the blood sample. By multiplying this dilution factor by a measurement value (concentration Z) of a target component to be analyzed in the diluted blood sample, it is possible to obtain a concentration [Z×(Y/X)] of the target component to be analyzed actually contained in the blood sample.

In addition, in order to verify whether diluting the blood, and separating and recovering the blood plasma are normally performed, it is preferable that with respect to two or more different normal components which are homeostatically present in the blood sample, dilution factors are separately obtained for each, and then it is confirmed whether values thereof match. The term "match" means, with respect to two measurement values (a, b), a ratio of their differences to their average values, that is, |a−b|/{(a+b)/2}×100 is 20% or smaller, preferably 10% or smaller, and more preferably 5% or smaller. As a preferred embodiment, a dilution factor is obtained from a measurement value of a concentration of sodium ions in a diluent solution of blood plasma of a blood sample and a known concentration value (142 mmol/liter) of sodium ions homeostatically contained in the blood plasma, and regarding the concentration analysis of a target component in the blood sample, which is performed using this dilution factor, by confirming that a dilution factor obtained from a normal component which is homeostatically contained in the blood plasma, other than sodium ions matches a dilution factor obtained from a concentration of sodium ions, it is possible to verify that analysis of the components contained in the blood plasma of the blood sample is normally performed. As examples of the normal component homeostatically present in blood plasma, other than sodium ions or chloride ions, it is preferably selected from total protein or albumins, and more preferably selected from total protein. Examples of a method for measuring total protein include the biuret method, the ultraviolet absorption method, the Bradford method, the Lowry method, the bicinchoninic acid (BCA) method, the fluorescence method, and the like, and it is possible to select a method to be used appropriately depending on characteristics, sensitivity, specimen amount, and the like of a measurement specimen.

In a second embodiment of the blood analysis method of the present invention, a dilution concentration is determined by using a normal component not present in the blood. In this case, blood plasma is recovered from the blood sample using a blood test kit including a diluent solution containing a normal component not present in the blood, the recovered blood plasma is diluted with the diluent solution, and a dilution factor of the diluted blood plasma is determined using the normal component not present in the blood, and therefore a concentration of a target component in the blood sample can be analyzed.

It is known that sodium in the blood has extremely a high level of homeostasis and variations among individuals are small. In addition, a concentration of a median value thereof is 142 mmol/L, which is high as a biological concentration, and therefore a concentration thereof can be measured at high accuracy even being diluted with a buffer solution. Furthermore, an internal standard in the buffer solution for dilution can be set to a high concentration, and therefore a concentration can be measured at high accuracy.

In a third embodiment of the blood analysis method of the present invention, blood plasma is recovered from the blood sample using a blood test kit including a diluent solution containing a normal component not present in the blood, the recovered blood plasma is diluted with the diluent solution, and a dilution factor of the diluted blood plasma is determined using the above-described normal component homeostatically present in the blood and the normal component not present in the blood, and therefore a concentration of a target component in the blood sample can be analyzed. By combining the measurement absorbance of the internal standard solution with the measurement absorbance of the external standard of the component having a high level of homeostasis of the specimen as described above, it is possible to complement the defects of the above two quantitative methods as a measurement method having high measurement accuracy, and therefore the method can be used as a quantification method for diluted components, which has high reliability.

It is preferable that a dilution ratio of the components of a blood sample is calculated by any one of Formulas 1 to 4, and a concentration of the target component to be analyzed in the diluent solution is multiplied by the above dilution ratio, and therefore a concentration of target component in the components of a blood sample is analyzed.

$$X=(A+C)/(B+D) \quad \text{Formula 1:}$$

$$X=\{(A^2+C^2)^{1/2}\}/\{(B^2+D^2)^{1/2}\} \quad \text{Formula 2:}$$

$$X=a\times(B+D)\pm b \quad \text{Formula 3:}$$

(a and b are coefficients, and a standard curve represented by Formula 3 is prepared in advance by acquiring data of (B+D) and a dilution factor)

$$X=A/B' \quad \text{Formula 4:}$$

$$(B'=(A\times D)/C)$$

In the above formulas, A, B, C, D, B', and X are defined as follows.
A: Measurement absorbance of the diluent solution containing an internal standard substance
B: Absorbance obtained by subtracting an absorbance of the diluent solution in which the blood plasma components is diluted from A
C: Measured absorbance of the solution in which a concentration of sodium ions, as a homeostatic substance, is 142 mmol/L
D: Absorbance of sodium ions in the diluent solution in which the blood plasma components is diluted
B': Correction value of an absorbance of a normal component not present in the blood in diluted blood plasma obtained by a dilution factor calculated from an absorbance of blood plasma sodium
X: Dilution factor of blood plasma As another calculation method for a case of obtaining a dilution ratio, an aspect in which a dilution ratio is calculated by Formula 5 using the root-mean-square method, a concentration of a target component to be analyzed in a diluent solution is multiplied by the dilution ratio calculated by Formula 5, and therefore a concentration of a target component in the components of a blood sample is analyzed, is preferable.

$$X=[\{(A/B)^2+(C/D)^2\}/2]^{1/2} \qquad \text{Formula 5:}$$

The present invention relates to the blood test kit for performing a test in which a patient performs blood collection and transports the collected blood to a medical institution or a test institution, and the blood analysis method using the blood test kit. Accordingly, from the blood collection to the test, there is a possibility that the blood is left alone for a long period of time in a diluted state. During the time, for example, red blood cells are hemolyzed, which leads to the release of substances, enzymes, and the like which are present at high concentration in the blood cells into the blood plasma or serum, and therefore a test result is affected thereby. Furthermore, in a case of measuring a target component to be analyzed by using tone, there is a possibility that hemoglobin affects the test. Therefore, it is necessary to prevent hemolysis, blood coagulation, and the like during transportation, and in the present invention, it is preferable to perform a step of separating blood cells from blood after diluting the blood collected by the patient with a diluent solution.

A method for separating blood cells from blood and recovering blood plasma is not particularly limited. The separation of blood plasma after blood collection is preferably carried out immediately after diluting the blood with a buffer solution. A method in which blood is collected with a blood collection tube container containing an anticoagulant, and then centrifuged to separate the blood into blood cells and blood plasma components, and transported in a separate state, or pressure is applied on the blood components so that the components pass through a separation membrane such as filtration membrane, the blood components are trapped with the separation membrane, and therefore the blood components are separated from the blood, and the like are used. In this case, it is preferable to use an anticoagulant. In addition, in order to ensure the accuracy of measurement, it is preferable to physically separate the blood plasma from the solution portion of the blood excluding blood cell components. In this case, specifically, it is possible to use a biological specimen-separation instrument having a backflow prevention means described in JP2003-270239A, and the like.

In the present invention, analyzing of a concentration of a target component in a blood sample includes determining a concentration of a target component (that is, quantifying a target component), determining whether a concentration of a target component is equal to or higher than a predetermined reference value or equal to or lower than a predetermined reference value, performing qualitative analysis for detecting that a certain amount of concentration is contained, and the like, and an embodiment of analysis is not particularly limited.

The target component to be analyzed is not limited, and any substance contained in a biological specimen is a target. Examples thereof include biochemical test items in blood used for clinical diagnosis, markers of various diseases such as tumor markers and hepatitis markers, and the like, and include proteins, sugars, lipids, low molecular weight compounds, and the like. In addition, not only a concentration of a substance is measured, but also an activity of a substance having an activity such as an enzyme is targeted. Measurement of each target component can be carried out by a known method.

An example of the blood analysis method of the present invention will be described below.

A blood specimen of a small volume of 65 μL was added to 280 μL of a buffer solution added with an internal standard and mixed, the blood cells were filtered through a filter, and using the diluted blood plasma as a specimen, each concentration of the internal standard, the external standard, and the biological component was measured using the automatic biochemistry analyzer.

According to one embodiment of the present invention, the method is a method in which, with respect to a large number of specimens, quantification and enzyme activity of diluted blood plasma biological specimen components of unknown concentration in the collected blood are efficiently analyzed by using a commercially available biochemical/automated immunoassay analyzer. An external standard substance that uses plasma sodium or the like maintaining a certain concentration in a biological specimen, or an internal standard substance which is a component that is not contained in or almost not contained in the blood plasma and which does not pass through the blood cell membrane is prepared, and are added to a buffer solution. It is preferable that the internal standard substance is stable in a diluent solution for a long period of time and can be easily quantitatively determined. Specific examples thereof include lithium and glycerol 3-phosphate. In addition, sodium which is an external standard of a measurement specimen is an element and thus is stable.

In a case of measuring sodium, it is possible to use an enzymatic assay by which sodium in several μL of specimen of very low sodium concentration (24 mmol/L or less) diluted with a diluent solution are measured by utilizing that the enzyme activity of the enzyme galactosidase is activated by sodium ions. In this method, a concentration of sodium in a specimen diluted with the diluent solution and β-galactosidase activity are in a proportional relationship. Therefore, the method can be applied to a biochemical/automated immunoassay analyzer, is highly efficient and economical for not required of another measuring instrument which is dedicated to sodium measurement, and thus is a particularly preferable measurement method.

The present invention will be described by the following examples, but the present invention is not limited by the examples.

EXAMPLE

Example 1

After informed consent was obtained from a volunteer patient, about 10 mL of blood collected from the vein by a syringe was obtained in a blood collection tube. A sponge capable of absorbing about 65 μL of blood was prepared, and using the DEMECAL (registered trademark) blood test kit (Leisure, Inc.) to which 300 μL of a diluted solution was added, analysis of GPT (glutamic pyruvate transaminase) and HbA1c (hemoglobin A1c) was performed. First, using the above-described kit, blood which is thought to be about 65 μL was aspirated using a blood collection instrument attached with the sponge prepared as described above, eluted in a diluent solution, and then stored in a container after blood plasma/blood cells separation was performed. Thereafter, the sample which was stored for three days in an environment of 25° C. to 40° C. without cooling was prepared while assuming that the bottle/sample was to be stored and transported in the summer. To a surface of the container, a thermo label capable of detecting an environment of 40° C. was affixed.

Separately, a case which is a horizontally long storing member having a thickness of 30 mm and including a space of the container to which the diluent solution of blood plasma after blood plasma/blood cells separation was added, and a space in which a cold insulator can be stored in adjacent states on both sides of the container, was prepared. The container to which the diluent solution of blood plasma after blood plasma/blood cells separation was added was stored thereto, in a form to be sandwiched by the cold insulator (ICE PACK: registered trademark) cooled from both sides thereof. A thermo label was affixed to the surface of the container to which the diluent solution of blood plasma was added. This case was sealed by putting the case in a heat shieldable cold insulated bag which has an aluminum film and can be shielded from light. This cold insulated bag was packaged in such a manner that the bag could be mailed, and then kept in the same environmental conditions for 3 days.

The thermo label of the container not using the cold insulation means displayed the history of 40° C. On the other hand, the thermo label of the container using the cold insulation means did not display the history of 40° C., and when the real temperature of the sample in a case of using the cold insulation means was measured, the temperature was 3° C. to 9° C.

Using the two prepared samples as described above, the maximum value and the minimum value of the blood analysis result and the coefficient of variation in a case where correcting of the dilution factor of the following (Method 1) to (Method 3) was performed were obtained. For the data in each correction method, the same experiment was repeated eight times, and statistical values were obtained.

(Method 1)

A concentration of sodium ions in the mixed solution after dilution was measured, from this value and a concentration value with respect to the concentration of sodium ions of 142 mmol/L, which is normally evaluated as a component homeostatically present in the blood, a dilution factor was calculated.

(Method 2) Using glycerol 3-phosphate added to the diluent solution, a dilution factor of blood plasma was obtained according to the method disclosed in "Clinicopathology Vol. 56, No. 7 (July 2008) Supplement 577-583".

(Method 3) A dilution factor was obtained according to the following method by using the dilution factor value obtained using Method 1 and Method 2.

(Method 3: Measurement of Dilution Factor by Combination of External Standard Method and Internal Standard Method)

Examples of the external standard method using sodium ions are described below. Table 1 shows measurement reagents for detecting sodium ions, which do not contain sodium ions.

TABLE 1

Compositions of reagents for measuring sodium ions

| | Reagent | Concentration |
|---|---|---|
| First reagent | pH 8.0, HEPES•LiOH | 100 mmol/L |
| | D-Mannitol | 60 mmol/L |
| | N-acetylcysteine | 30 mmol/L |
| | Magnesium sulfate | 1.52 mmol/L |
| | β-galactosidase | 1.1 kU/L |
| | TRITON (registered trademark) X-100 | 0.05% by mass |
| Second reagent | pH 8.0, HEPES•LiOH | 100 mmol/L |
| | o-Nitrophenyl β-D-galactopyranoside | 15 mmol/L |

Figure 3:
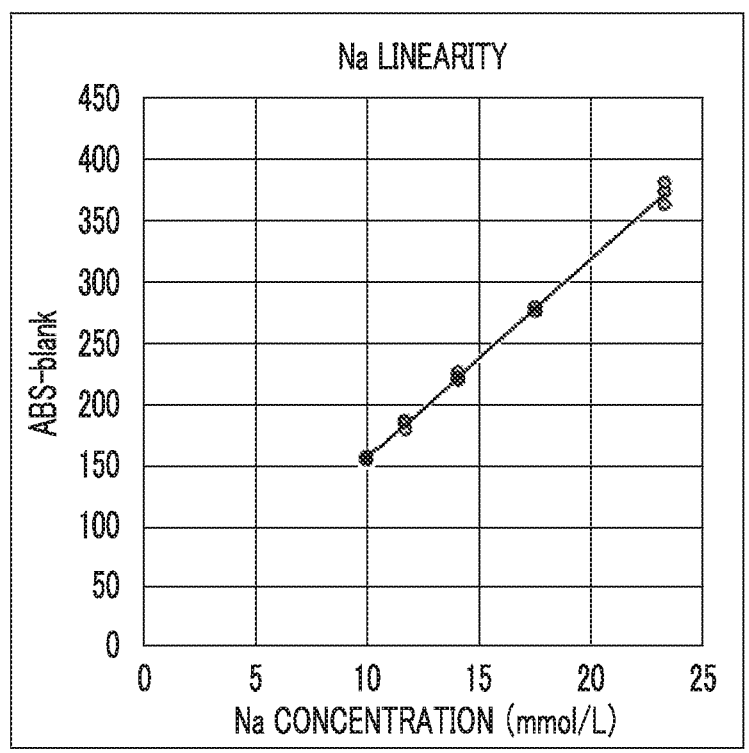
FIG. 3 illustrates the linearity in a sodium enzymatic assay.

If whole blood of 65 μL was added to 280 μL of the diluent solution, blood plasma (about 30 μL) in the whole blood is diluted about 10 times. To 3 μL obtained by diluting the diluted blood plasma 5 times with purified water, 52 μL of the first reagent which is a reagent for measuring sodium ions was added and heat-insulated at 37° C. for 5 minutes, and then 26 μL of the second reagent which is a reagent for measuring sodium ions was added. The change in absorbance was measured during 1 minute at a main wavelength of 410 nm and a complementary wavelength of 658 nm by using JCA-BM6050-type automatic biochemistry analyzer (manufactured by JEOL Ltd.). The concentration of sodium ions was measured from a calibration curve prepared in advance. As a result of preparing a calibration curve indicating the concentration of sodium ions and change in absorbance, linearity passing through the origin point was obtained up to 24 mmol/L, and sodium quantitativeness was confirmed as shown in FIG. 3.

Table 2 illustrates compositions of a diluent solution to which an internal standard is added and which does not contain sodium ions. As osmotic pressure, a value measured by using OSMOATAT OM-6040 (manufactured by ARKRAY, Inc.) is shown.

TABLE 2

| Substance name | Concentration |
|---|---|
| HEPES | 50 mmol/L |
| 2-Amino-2-methyl-1-propanol (AMP) | 50 mmol/L |
| D-Mannitol | 284 mmol/L |
| Glycerol 3-phosphate | 5 mmol/L |
| EDTA-2K | 0.8 mmol/L |
| PALP (pyridoxal phosphate) | 0.05 mmol/L |
| Thiabendazole | 0.0001% by mass |
| Piperacillin sodium | 0.0003% by mass |
| Amikacin sulfate | 0.0003% by mass |
| Kanamycin sulfate | 0.0005% by mass |
| Meropenem trihydrate | 0.0005% by mass |
| Osmotic pressure | 355 mOsm/Kg |
| pH 7.4 | |

By using a concentration of glycerol 3-phosphate which is an internal standard substance, and a concentration of sodium ions which is a homeostatic substance, a dilution factor (X) was obtained from Formula (1) by using JCA-BM6050-type automatic biochemistry analyzer (manufactured by JEOL Ltd.).

$$X[\{(A/B)^2+(C/D)^2\}/2]^{1/2} \qquad (1)$$

A: Measurement absorbance of the diluent solution containing glycerol 3-phosphate B: Absorbance obtained by subtracting an absorbance of the mixed solution in which blood plasma components of blood and the diluent solution are mixed, from the absorbance of A C: Measured absorbance of a solution in which a concentration of sodium ions, as a homeostatic substance, is 142 mmol/L D: Absorbance of a concentration of sodium ions in the diluent solution by which the blood plasma components are diluted X: Dilution factor of blood plasma A concentration of the biochemical component in the diluted plasma can be obtained by multiplying the measurement value of a concentration of the reaction product utilizing the known enzyme activity by the dilution factor obtained by Formula (1), and therefore the biochemical component in the original blood plasma was quantitatively determined.

Regarding the quantitatively determined value of GPT and HbA1C obtained by using a dilution factor calculated by Method 1 to Method 3, the maximum value, the minimum value, and the coefficient of variation CV (coefficient of variation: %) are shown in Table 3.

TABLE 3

| | Cooling | Test item | Maximum value GPT (U/L) HbA1C (%) | Minimum value GPT (U/L) HbA1C (%) | Difference GPT (U/L) HbA1C (%) | Coefficient of variation CV (%) | |
|---|---|---|---|---|---|---|---|
| Method 1 | Not performed | GPT | 16.1 | 12.1 | 4.0 | 13.0 | Comparative Example 1 |
| | Performed | GPT | 15.5 | 13.9 | 1.6 | 5.3 | Example 1 |
| Method 2 | Not performed | GPT | 15.3 | 12.2 | 3.1 | 10.9 | Comparative Example 2 |
| | Performed | GPT | 15.3 | 14.2 | 1.1 | 4.6 | Example 2 |
| Method 3 | Not performed | GPT | 15.2 | 12.2 | 3.0 | 8.4 | Comparative Example 3 |
| | Performed | GPT | 15.0 | 14.4 | 0.6 | 3.1 | Example 3 |
| Method 1 | Not performed | HbA1C | 5.2 | 4.5 | 0.7 | 5.6 | Comparative Example 4 |
| | Performed | HbA1C | 5.2 | 4.8 | 0.4 | 2.9 | Example 4 |
| Method 2 | Not performed | HbA1C | 5.1 | 4.5 | 0.6 | 4.5 | Comparative Example 5 |
| | Performed | HbA1C | 5.2 | 4.9 | 0.3 | 2.0 | Example 5 |
| Method 3 | Not performed | HbA1C | 5.1 | 4.2 | 0.9 | 7.3 | Comparative Example 6 |
| | Performed | HbA1C | 5.1 | 4.9 | 0.2 | 1.6 | Example 6 |

As shown in Table 3, a decrease of the difference between the maximum value and the minimum value, and the coefficient of variation (CV %) of the measurement is confirmed according to the configuration of the present invention, and it was possible to confirm the effect that each measurement accuracy is high.

Example 2

After blood collection, the blood plasma/blood cells separating instrument of the DEMECAL blood test kit (Leisure, Inc.) was used when diluting with the buffer solution, and blood plasma/blood cells separation was performed immediately after the dilution. Next, as in Example 1, a case with a thickness of 30 mm which can be kept cold was prepared, packaged in such a manner that the bag could be mailed after being kept cold as in Example 1, imparted with the equivalent vibration at the time of 2,500 km land transportation within the country, and then blood analysis was carried out at 25° C. after 3 days.

A dilution factor was determined using Method 1 or 3 described in Example 1. GOT (glutamic acid oxaloacetate transaminase), HbA1C and CRE (creatinine) were measured as the test items.

As a comparison, immediately after blood dilution, without carrying out blood plasma/blood cells separation, the bag was stored in the coolable case similarly, packaged in the same manner, imparted with the equivalent vibration at the time of 2,500 km land transportation within the country, and then after 3 days, the blood specimen was centrifuged at 25° C. to perform blood plasma/blood cells separation, and then blood analysis was carried out.

The average value of the quantitatively determined results and the coefficient of variation % are shown in Table 4.

TABLE 4

| | | Test item | Average value GOT (U/L) HbA1C (%) CRE (mg/L) | Coefficient of variation CV (%) | |
|---|---|---|---|---|---|
| Method 1 | Analyzed 3 days after blood plasma/blood cells separation performed immediately after blood dilution | GOT | 34.9 | 3.0% | Example 7 |
| | | HbA1C | 5.1 | 3.7% | |
| | | CRE | 0.13 | 1.5% | |
| | Analyzed after blood plasma centrifugation 3 days after dilution | GOT | 37.4 | 4.3% | Example 8 |
| | | HbA1C | 6.3 | 4.5% | |
| | | CRE | 0.145 | 1.8% | |
| Method 3 | Analyzed 3 days after blood plasma/blood cells separation performed immediately after blood dilution | GOT | 35.1 | 2.0% | Example 9 |
| | | HbA1C | 5.1 | 2.2% | |
| | | CRE | 0.13 | 0.9% | |
| | Analyzed after blood plasma centrifugation 3 days after dilution | GOT | 37.2 | 3.3% | Example 10 |
| | | HbA1C | 6.2 | 3.9% | |
| | | CRE | 0.14 | 1.6% | |

As a result of the case of keeping the bag cold, the difference of variation in the case of performing the blood plasma/blood cells separation or not is small, but by performing the blood plasma/blood cells separation immediately after diluting the blood sample, the influence of transport vibration was slightly reduced, and it was found that analysis results with less variation can be obtained.

Example 3

An example of a method for determining the dilution factor of blood plasma is shown. In the compositions of Table 2, a diluent solution to which an internal standard is added and which does not contain sodium ions in which glycerol 3-phosphate was changed to 1 mmol/L of lithium chloride, was prepared. Measurement of the lithium internal standard substance added to the buffer solution can be carried out by measuring the absorbance by the chelate colorimetric method (halogenated porphyrin chelating method: perfluoro-5,10,15,20-tetraphenyl-21H,23H-porphyrin).

As described above, the dilution factor of the blood plasma with the buffer solution can be obtained by Formula (2).

$$X=(A+C)/(B+D) \quad (2)$$

A: Measurement absorbance of the diluent solution containing lithium
B: Absorbance obtained by subtracting an absorbance of the diluent solution by which blood plasma components are diluted from A
C: Measured absorbance of a solution in which a concentration of sodium ions, as a homeostatic substance, is 142 mmol/L
D: Absorbance of a concentration of sodium ions in the diluent solution by which the blood plasma components are diluted
X: Dilution factor of blood plasma Using blood collected from a plurality of patients of which blood clotting was prevented by adding EDTA as a specimen, in the same manner as Example 1, a container to which the blood plasma diluent solution was added after blood plasma/blood cells separation was sandwiched between a cold insulator so as to be stored, and a container to which the blood plasma diluent solution affixed with the thermo label on the surface thereof was added and sealed in a light-shielding cold insulated bag with aluminum film. This cold insulated bag was packaged in such a manner that the bag could be mailed, and then kept in the same environmental conditions of 25° C. to 40° C. for 3 days. Thereafter, the biochemical components in the diluted blood plasma was measured, the dilution factor of the blood plasma was calculated using Formula (2), and the value (A) of the biochemical component contained in the blood plasma was calculated. Separately, the same blood specimen was collected by adding EDTA and subjected to centrifugation, and blood cells were separated to obtain blood plasma, and the blood plasma was used without being diluted, and therefore the value (B) of the biochemical component was measured. Correlation coefficients of the obtained values were calculated using Formula (3).

Correlation coefficient=(covariance of value (A) and value (B))/{(standard deviation of value (A))× (standard deviation of value (B)} (3)

The closer the correlation coefficient is to 1.000, the more consistent the two data, and generally 0.800 or more shows good correlation. In addition, a regression equation (y=ax±b) was obtained by preparing a scattergram from the two data and using a least squares method as a statistical formula of the distribution. The symbol "a" indicates that the proportionality of the two data is good within the range of 0.95 to 1.05 in the slope of the regression equation. Furthermore, the symbol "b" indicates that the error is small when the intercept of the regression equation is close to a numerical value of 0. The results are shown in Table 5. Based on the results in Table 5, it was found that the correlation between diluted blood plasma and blood plasma was a good result.

TABLE 5

Correlativity between blood plasma and diluted blood plasma in internal and external standard method

| Item | Correlation coefficient | Regression formula (y = ax ± b) |
| --- | --- | --- |
| Total protein | 0.751 | y = 0.98x + 1.4 |
| Albumins | 0.822 | y = 0.97x + 0.6 |
| AST (aspartate aminotransferase) | 0.990 | y = 0.98x + 0.5 |
| ALT (alanine transaminase) | 0.998 | y = 1.00x − 0.1 |
| γ-GTP (γ-glutamyl transpeptidase) | 0.998 | y = 1.02x − 0.6 |
| Total cholesterol | 0.973 | y = 0.97x + 5.6 |
| HDL (high density lipoprotein) cholesterol | 0.987 | y = 0.97x + 1.5 |
| LDL (low density lipoprotein) cholesterol | 0.990 | y = 0.98x + 3.3 |
| Neutral fat | 0.999 | y = 1.05x − 3.8 |
| Urea nitrogen | 0.993 | y = 0.99x + 0.1 |
| Creatine | 0.966 | y = 0.98x + 0.0 |
| Uric acid | 0.994 | y = 1.01x + 0.0 |
| Glucose | 0.994 | y = 0.97x + 2.0 |

Example 4

In Example 1, in addition to the measurement of a concentration of sodium ions, a concentration of total protein was measured with respect to the blood plasma diluent solution stored in the container using the cold insulation means, by a method described below.

(Measurement of Total Protein Concentration in Blood Plasma Diluent Solution)

Measurement was performed with the buret method as the measurement principle. Biuret reagent: 3.0 mmol/L, copper sulfate 400 μL, potassium sodium tartrate 21.3 mmol/L, and NaOH 0.75 mmol/L were prepared and mixed with the blood plasma diluent solution. After mixing, the solution was allowed to stand at 37° C. for 10 minutes, it was waited until a complex exhibiting a blue-violet color of 540 to 560 nm due to protein and copper ions in the blood plasma diluent solution is formed under the alkaline condition, and an absorbance was measured at 545 nm. The concentration of total protein in the blood plasma diluent solution was quantitatively determined using a calibration curve obtained from the absorbance of a standard solution.

The results was obtained, in which with respect to the dilution factor of the blood sample, which was calculated from the measurement value of the concentration of sodium ions in the blood plasma diluent solution and the average value of 142 mmol/L of the concentration of sodium ions homeostatically contained in the blood sample, the dilution factor in the diluent solution after diluting blood, which was obtained from the measurement value of the total protein and the average value of 7.5 g/100 mL of the concentration of sodium ions homeostatically contained in the total protein which is the normal component in the blood sample was the same value. Based on this, it was found that the measurement using the dilution factor obtained from the concentration of sodium ions was performed normally, and it was found that the measurement could be verified.

Example 5

Figure 2:
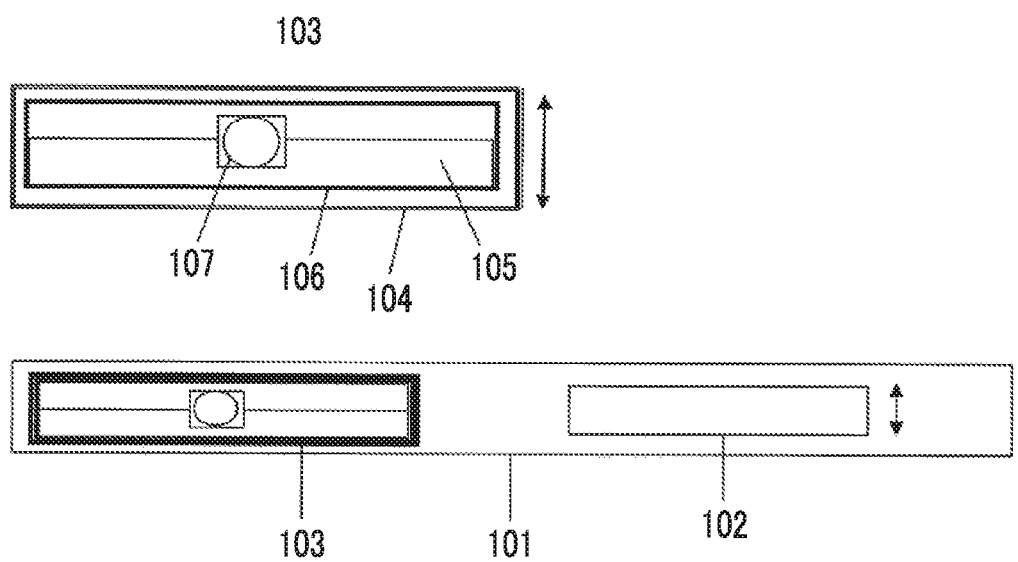
FIG. 2 illustrates a schematic diagram of a moistureproof case.

A moistureproof case (the outside made of paper that can be printed or typed) having an outer shape of 21.0 cm×17.0 cm×3.4 cm, in which an aluminum moistureproof film is laminated was prepared as a return container of the DEMECAL blood test kit (Leisure, Inc.), from the viewpoint of light shielding, thermal insulation, and prevention of leakage of diluted blood plasma. FIG. 2 illustrates a schematic diagram of the moistureproof case on the lower part of the drawing. In a moistureproof case 101, a package 102 of the DEMECAL kit and a cold insulator-containing case 103 for returning were stored to be returned.

The cold insulator-containing case 103 for returning (the upper part in FIG. 2) will be described below. As shown in the overview on the upper part of FIG. 2 as a rectangular parallelepiped having an outer shape of 10.0 cm×16.5 cm×2.8 cm (the arrow in the drawing is about 2.8 cm) inside the aluminum film 104, a non-solidifying cold insulator 105 consisting of water and high water-absorption resin (sodium polyacrylate), a preservative, and a shape stabilizer, was added to a resin bag 106 having a moisture-proof and cushioning property so as to be processed. A space 107 for storing a columnar bottle having a diameter of 16 mm and a height of 7.7 mm, after separating blood plasma was provided on the center of the bag. The bottle was stored in the space 107 so as to be sandwiched by the cold insulator, and furthermore, a cold insulation pack capable of being folded into two which can be stored in the moistureproof case for returning was prepared. When the temperature inside the bottle at the time of cooing was measured by laminating a RF (radio frequency) tag equipped with a temperature sensor to the surface of the bottle, the temperature was 6° C.

In this packaging form, the moistureproof case in which a blood collection sample and the DEMECAL blood test kit used were stored was put into a mailbox so as to be mailed.

EXPLANATION OF REFERENCES

1: blood separating instrument
2: blood collection container
3: tubular body
4: cap piston
5: sealing lid
6: cap
7: packing
8: screw portion
9: locking portion
10: bottom portion
11: leg portion
12: slit grooves
13: diluent solution
14: expanded diameter section
15: thin wall portion
16: main body portion
18: reduced diameter section
19: protruded locking portion
20: outer flange portion
21: filtration membrane
22: cover
26: knob portion
27: mandrel portion
28: space
29: lower end portion
31: level difference portion
33: upper end portion
34: top portion
101: moistureproof case
102: package
103: cold insulator-containing case for transportation
104: aluminum film
105: cold insulator
106: resin bag
107: space

What is claimed is:

1. A blood test kit, comprising:
a diluent solution for diluting a blood sample;
a blood separating instrument which comprises a blood collection container, a tubular body capable of being to fit into the blood collection container so as to be inserted, a cap piston capable of being capped on the tubular body, and a sealing lid provided at a lower end of the cap piston, for recovering blood plasma components from the diluted blood sample, with a combination of said blood collection container and said tubular body constituting a container for storing the blood plasma components recovered from the diluted blood sample; and
a cold insulated bag containing a cold insulator for cold-insulating the container,
wherein the diluent solution does not contain sodium ions.

2. The blood test kit according to claim 1,
further comprising a storing member having a thickness of 35 mm or less, the storing member storing the cold insulated bag and the container for storing the recovered blood plasma components.

3. The blood test kit according to claim 1, further comprising:
a temperature history recorder which comprises a temperature-detectable thermo label or a temperature sensor.

4. The blood test kit according to claim 1, further comprising:
a manual describing a method for using the cold insulated bag containing a cold insulator.

5. The blood test kit according to claim 1,
wherein the blood test kit is a blood test kit for analyzing a concentration of a target component in the blood sample by using a normal component homeostatically present in blood, and
the diluent solution does not contain the normal component.

6. The blood test kit according to claim 5,
wherein the normal component is sodium ions or chloride ions.

7. The blood test kit according to claim 5,
wherein the normal component is sodium ions or chloride ions, and total protein or albumins.

8. The blood test kit according to claim 7,
wherein the blood test kit is a blood test kit for analyzing a concentration of the target component in the blood sample by using the normal component homeostatically present in blood, and verifying the analysis.

9. The blood test kit according to claim 1,
wherein the diluent solution contains a normal component not present in blood, and the blood test kit is a blood test kit for analyzing a concentration of the target component in the blood sample by using the normal component not present in blood.

10. A blood analysis method using the blood test kit according to claim 5, the method comprising the following steps of:
   recovering blood plasma from a blood sample;
   diluting the recovered blood plasma with a diluent solution;
   determining a dilution factor of the blood plasma by using a normal component homeostatically present in blood, which is contained in the diluted blood plasma; and
   analyzing a concentration of a target component in the blood sample.

11. The blood analysis method according to claim 10, the method further comprising the following steps of:
   determining the dilution factor of the blood plasma by using a normal component different from the normal component homeostatically present in blood; and
   verifying the analysis of a concentration of the target component.

12. A blood analysis method using the blood test kit according to claim 9, the method comprising the following steps of:
   recovering blood plasma from a blood sample;
   diluting the recovered blood plasma with a diluent solution;
   determining a dilution factor of the blood plasma by using a normal component not present in blood, which is contained in the diluted blood plasma; and
   analyzing a concentration of a target component in the blood sample.

13. The blood analysis method according to claim 12, the method comprising the following steps of:
   determining a dilution factor of the blood plasma by using a normal component homeostatically present in blood, and the normal component not present in blood which is contained in the diluted blood plasma; and
   analyzing a concentration of a target component in the blood sample,
   wherein the diluent solution included in the blood test kit does not contain the normal component homeostatically present in blood.

14. The blood analysis method according to claim 10, wherein a liquid volume of the diluted blood plasma is 100 µL or more and 1000 µL or less.

15. The blood analysis method according to claim 12, wherein a liquid volume of the diluted blood plasma is 100 µL or more and 1000 µL or less.

16. The blood analysis method according to claim 13, wherein a liquid volume of the diluted blood plasma is 100 µL or more and 1000 µL or less.

17. The blood test kit according to claim 1, wherein the diluent solution contains glycerol 3-phosphate or lithium chloride, but does not contain sodium ions.

18. The blood test kit according to claim 1, wherein the blood separating instrument further comprises a filter having fine pores capable of separating blood cell components.

* * * * *